(12) United States Patent
Pettit et al.

(10) Patent No.: US 7,078,552 B2
(45) Date of Patent: Jul. 18, 2006

(54) COMBRETASTATIN A-1 PHOSPHATE AND COMBRETASTATIN B-1 PHOSPHATE PRODRUGS

(75) Inventors: George R. Pettit, Paradise Valley, AZ (US); John W. Lippert, III, Tempe, AZ (US)

(73) Assignee: Arizona Board of Regents, Tempe, AZ (US); acting for and on behalf of Arizona State University ( * ) Notice: Subject to any disclaimer, the term of this patent is extended or adjusted under 35 U.S.C. 154(b) by 157 days.

(21) Appl. No.: 10/258,672

(22) PCT Filed: Apr. 27, 2001

(86) PCT No.: PCT/US01/13858

§ 371 (c)(1),
(2), (4) Date: Oct. 25, 2002

(87) PCT Pub. No.: WO01/81355

PCT Pub. Date: Nov. 1, 2001

(65) Prior Publication Data

US 2003/0220298 A1  Nov. 27, 2003

Related U.S. Application Data

(60) Provisional application No. 60/200,395, filed on Apr. 27, 2000.

(51) Int. Cl.
*C07F 9/02* (2006.01)

(52) U.S. Cl. .................... 558/166; 558/190; 556/13; 556/24; 514/143

(58) Field of Classification Search ................ 558/166, 558/190; 556/13, 24
See application file for complete search history.

(56) References Cited

U.S. PATENT DOCUMENTS

| 5,409,953 | A | 4/1995 | Pettit et al. |
| 5,561,122 | A | 10/1996 | Pettit |
| 5,569,786 | A | 10/1996 | Pettit et al. |
| 6,538,038 | B1 | 3/2003 | Pero et al. |

FOREIGN PATENT DOCUMENTS

| WO | WO 92/16486 A1 | 10/1992 |
| WO | WO 99/34788 A1 | 7/1999 |
| WO | WO 99/35150 A1 | 7/1999 |
| WO | WO 00/48590 A1 | 8/2000 |
| WO | WO 00/48606 A1 | 8/2000 |
| WO | WO 2001081355 | * 1/2001 |

OTHER PUBLICATIONS

Shnyder, S.D et al Anticancer Research (2003) 23 (2B) 1619–1628.*
Holwell S.E. et al Anticancer Research (2002) 22 (6C) 3933–3940.*
Holwell, S.E. et al Anticancer Research (2002) 22(2A) 707–711.*
Pettit, G. R. et al., Atnineoplastic agents 429. Syntheses of the Combretastatin A–1 and Combretastatin B–1 Prodrugs. Anti–Cancer Drug Design. May 2000, vol. 15, pp. 203–216.
Pettit, G.R. et al., Antineoplastic agents 440. Astnnetruc Syntheses and Evaluation of the Combretastatin A–1 SAR Probles (1S,2S)–and (1R,2R)–1,2–Dihydrozy–1–(2', 3'–dihydroxy–4'–methoxyphenyl)–2–(3",4",5"–trimethoxyphenyl)–ethane. J. Nat. Prod., Jun. 30, 2000, vol. 63, pp. 969–974.
Pettit, G.R. et al. Antineoplastic Agents 443. Synthesis of the Cancer Cell Growth Inhibitor Hydroxyphenstatin and Its Sodium Diphosphate Prodrug. J. Med. Chem. Jun. 24, 2000, vol. 43, pp. 2731–2737.

* cited by examiner

Primary Examiner—Paul J. Zucker
(74) Attorney, Agent, or Firm—Fennemore Craig, P.C.

(57) ABSTRACT

The present invention relates to the syntheses and structural elucidation of Combretastatin A1-Phosphate Prodrugs and Combretastatin B1-Phosphate Prodrugs and the utilization of those prodrugs in the treatment of neoplastic diseases. The prodrugs described herein have the structure: Combretastin A-1 Phosphate Prodrug (I) and Combretastin B-1 Phosphate Prodrug (II).

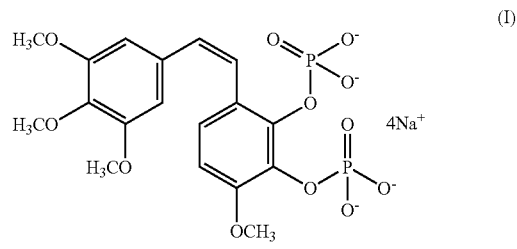

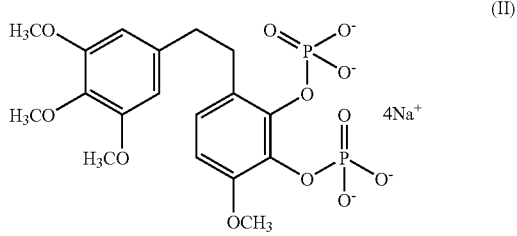

39 Claims, No Drawings

COMBRETASTATIN A-1 PHOSPHATE AND COMBRETASTATIN B-1 PHOSPHATE PRODRUGS

This application is a U.S. national stage PCT application of PCT/US01/13858 filed on Apr. 27, 2001, which claims the priority of U.S. Provisional Application Ser. No. 60/200,395 filed on Apr. 27, 2000.

INTRODUCTION

The present invention relates generally to the syntheses and structural elucidation of Combretastatin A-1 Phosphate Prodrug and Combretastatin B-1 Phosphate Prodrug, and to the treatment of neoplastic diseases therewith.

This research was funded in part by Outstanding Investigator Grant CA4434-05-10 awarded by the National Cancer Institute, DHHS. The United States government may have certain rights to this invention.

BACKGROUND OF THE INVENTION

In 1987, the isolation and synthesis of combretastatin A-1 (1) and B-1 (2) from the South African willow tree *Combretum caffrum* (Combretaceae) was reported (Pettit et al, 1987). Both natural products were shown to be significant cancer cell growth inhibitors and antimitotic agents, providing an $ED_{50}$ value of 0.99 µg/ml and 1.7 µg/ml respectively against the murine P388 lymphocytic leukemia in vitro system, and inhibiting microtubule assembly in vitro with $IC_{50}$ values of 2 µM (1) and 3 µM (Pettit et al, 1987). A comparison of diphenol 1 to the monophenol counterpart combretastatin A-4 (3a), the most active anticancer member of the combretastatin family, revealed a very similar antimitotic activity ($IC_{50}$ 2–3 µM, but much greater cytotoxicity ($ED_{50}$~0.0009 µg/ml, P388 cell line) (3a) (Pettit et al, 1989). However in early murine (P388 leukemia) in vivo experiments, combretastatin A-1 led to more consistent antineoplastic results (Pettit et al, 1987). The relevant structures are shown in Figure 1, below.

Figure 1

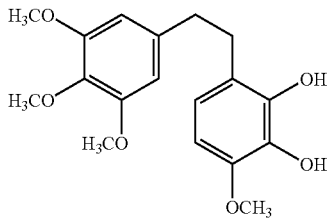

2, Combretastatin B-1

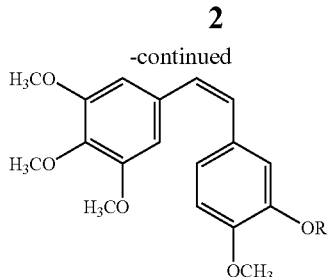

3a, R = H, Combretastatin A-4
3b, R = P(O)(OCH$_2$C$_6$H$_5$)$_2$
3c, R = P(O)(O$^-$Na$^+$)$_2$ Development of combretastatin A4 to the current Phase I human cancer clinical trials was accelerated following synthesis of the phosphate prodrug 3c from dibenzyl phosphate 3b and then uncovering its very promising cancer antiangiogenesis effects. The phosphate derivative was chosen due to the nature of its biolability and enhanced solubility characteristics. Once administered, the phosphate prodrug is presumed to be converted into the parent drug via non-specific phosphatases and then transported intracellularly. Phosphate 3c showed similar cytotoxicity when compared to the parent compound ($GI_{50}$ 0.0004 µg/ml, P388 cell line), while greatly increasing the aqueous solubility to 20 mg/ml. Prodrug 3c was also shown to induce vascular shutdown within murine metastatic tumors at doses less than one-tenth of the maximum tolerated dose.

The preclinical development of combretastatin A-1 (1) was hampered owing to instability (oxidation to the 1,2-quinone) (Sackett, 1993; Haines, 1988) of the 2,3-dihydroxy unit. This was supported by the fact that acetylation of 1 significantly enhanced cytotoxicity 10-fold, while reducing the inhibition of the tubulin assembly.

The synthesis of the combretastatin A-1 and B-1 phosphate prodrugs were undertaken in order to improve solubility for drug delivery and to increase stability. Thus, the present invention is directed to the syntheses of combretastatin A-1 prodrug ($ED_{50}$<0.0100 µg/ml, P388 cell line, 4), combretastatin B-1 prodrug ($ED_{50}$ 0.335 µg/ml, P388 cell line, 5), as shown in Scheme 1, below, and a series of metal cation and ammonium cation salts of the diphosphoric acid precursor 4 to evaluate effects on in vitro human cancer cell growth and solubility behavior.

Scheme 1

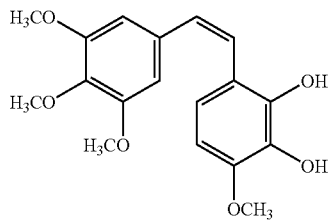

1, Combretastatin A-1

(BnO)$_2$P(O)H
CH$_3$CN, CCl$_4$, DMAP
DIPEA, -20° C.

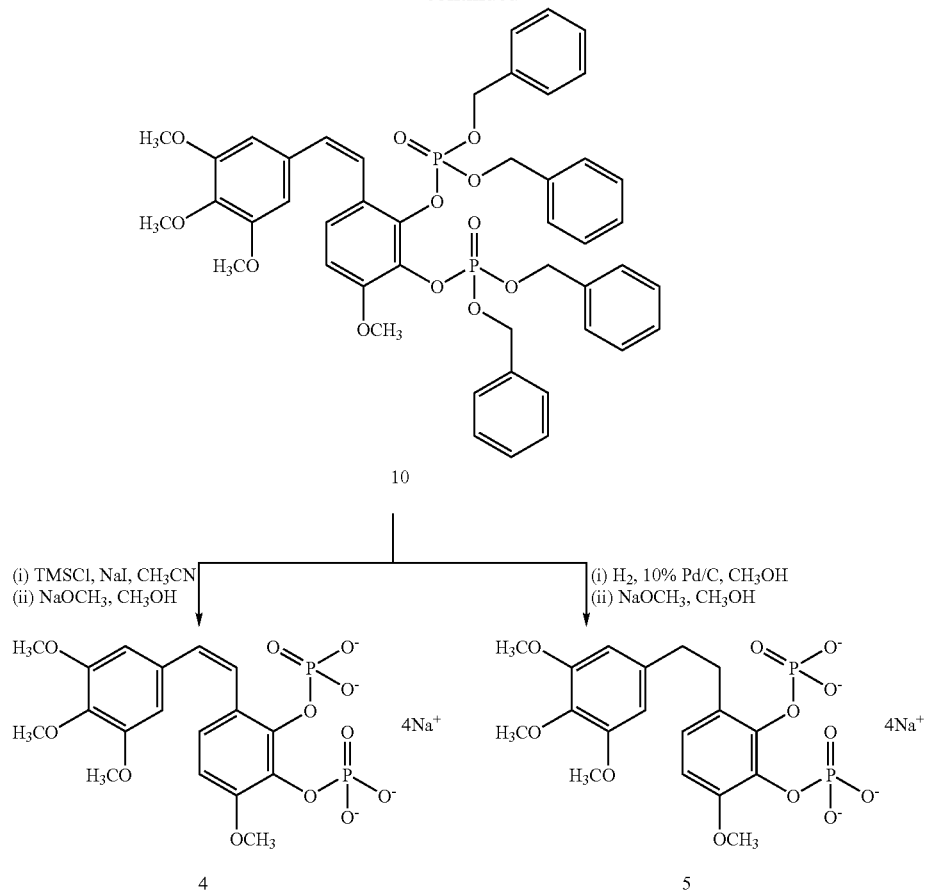

BRIEF SUMMARY OF THE INVENTION

The original synthesis of combretastatin A-1 (1) was greatly improved to allow an efficient scale-up procedure for obtaining the antineoplastic stilbene. Subsequent conversion to a useful prodrug was accomplished by diphosphorylation (to 10) with in situ formation of dibenzylchlorophosphite followed by cleavage of the benzyl ester protecting groups with trimethyliodosilane. The phosphoric acid intermediate was treated with sodium methoxide to complete a practical route to the sodium phosphate prodrug (4). Selective hydrogenation of phosphate 10 and treatment of the product with sodium methoxide led to combretastatin B-1 phosphate prodrug (5). The phosphoric acid precursor of prodrug 4 was employed in a parallel series of reactions to produce a selection of metal and ammonium cation prodrug candidates. Each of the phosphate salts was evaluated from the perspective of relative solubility behavior and cancer cell growth inhibition. The sodium phosphate prodrug (4) of combretastatin A-1 was selected for detailed antineoplastic studies.

Accordingly, the primary object of the present invention is the discovery of phosphate prodrugs, which have been shown to exhibit greatly improved properties in vitro and are designated herein as the combretastatin A-1 phosphate prodrugs and combretastatin B-1 phosphate prodrug.

Another object of the present invention is the synthesis of metal and ammonium cation derivatives of combretastatin A-1 2',3'-O-diphosphate through the appropriate acid-base reaction.

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

Materials and Methods

Ether refers to diethyl ether. All solvents were redistilled. Boron trichloride (1.0 M solution in $CH_2Cl_2$), triphenylphosphine, tetrabutylammonium fluoride (1.0 M solution in THF), dibenzyl phosphite, diisopropylethylamine (99%), chlorotrimethylsilane (99%), 4-dimethylaminopyridine (DMAP), carbon tetrachloride (99%), zinc acetate dihydrate, papavarine, and cesium hydroxide were obtained from Sigma-Aldrich Chemical Company (Milwaukee, Wis.). Magnesium acetate tetrahydrate, calcium acetate, manganese acetate, quinidine, quinine, and concentrated hydrochloric acid were obtained from the Baker Chemical Company. Verapamil and nicotinamide were purchased from the Alexis Corporation. All other reagents were purchased from Acros Organics (Fisher Scientific, Pittsburgh, Pa.).

Reactions were monitored by thin-layer chromatography using Analtech silica gel GHLF Uniplates visualized under long-wave and short-wave UV irradiation. Solvent extracts of aqueous solutions were dried over anhydrous sodium sulfate. Where appropriate, the crude products were sepa rated by column chromatography, flash (230–400 Mesh ASTM) or gravity (70–230 Mesh ASTM) silica from E. Merck.

Melting points were measured with an electrothermal digital melting point apparatus (model IA9200) and are uncorrected. The IR spectra were obtained using a Mattson Instruments 2020 Galaxy Series FT-IR EIMS data were recorded with a MAT 312 mass spectrometer, and high-resolution FAB spectra were obtained with a Kratos MS-50 mass spectrometer (Midwest Center for Mass Spectrometry, University of Nebraska, Lincoln, Nebr.). TOFMS data were recorded with a Vestec Lasertec Research mass spectrometer incorporating a Laser Sciences nitrogen laser that provided 337 nm light pulses of 3 ns duration with 4-hydroxybenzylidenemalononitrile as the matrix and cytochrome c as the external standard for calibration purposes. Optical rotation values were recorded employing a Perkdn Elmer 241 polarimeter. The UV spectra were recorded using a Hitachi U-2000 UV/VIS spectro-photometer. All $^1$H and $^{13}$C NMR spectra were obtained using a Varian Gemini 300 MHz instrument with CDCl$_3$ (TMS internal reference) as solvent unless otherwise noted. The $^{31}$P NMR spectra were obtained in CDCl$_3$, or D$_2$O with 85% H$_3$PO$_4$ as an external standard employing a Unity 500 MHz instrument. Elemental analyses were determined by Galbraith Laboratories, Inc., Knoxville, Tenn.

Upon initiation of this investigation directed at obtaining a useful prodrug of combretastatin A-1 (1), synthesis (Pettit et al, 1987) of the parent compound required modification for a suitable scale-up procedure. Three major improvements were needed: a more economic synthesis of 2,3-dihydroxy4-methoxy-benzaldehyde (6b); better separation of the bis-(TBDMS) cis- and trans-isomers (8 and 9a) produced in the Wittig reaction; and efficient desilyation of 8 to diphenol 1. A better route to aldehyde 6b was found to involve selective demethylation of 2,3,4-trimethoxybenzaldehyde (6a) using a 1.0 M solution of boron trichloride in dichloromethane (Kaisalo et al, 1986). This method gave yields consistently in the 70% range, and the reaction was conducted in a solvent that facilitated isolation of the water-soluble diphenol (6b). The Wittig reaction sequence earlier used to afford stilbenes 8 and 9a relied on the separation by fractional recrystallization in ethanol. Both of these compounds were efficiently separated in the present study by column chromatography (60:1:1, hexane:ethyl acetate:triethylamine). As expected, cis-isomer 8 was easily converted to trans-isomer 9a by photoisomerization in high yield (>80%) using 366 nm light (Waldeck, 1991; Pettit & Singh, 1987). Finally, the desilylation of cis-isomer 8 to combretastatin A-1 (1) using tetrabutylammonium fluoride (TBAF) as originally described proved to be unsatisfactory on a larger scale owing to formation of polymeric products. However, diphenol 1, a base-sensitive catechol, was obtained in good yields under acidic cleavage conditions employing 48% HBr (cat.) and potassium fluoride in N,N-dimethylformide (Sinhababu et al, 1988; Nelson & Crouch, 1996). Although the crude product produced from the original TBAF desilylation procedure could be used directly in the phosphorylation step to afford phosphate 10, it did not prove useful for obtaining pure combretastatin A-1 (1) by column chromatography. trans-Stilbene 9a was also readily desilylated using either the 48% HBr (cat.)/KF or the TBAF method to afford previously unreported diphenol 9b. The relevant structures are shown in Figure 2, below.

Figure 2

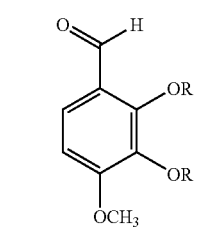

6a, R = CH$_3$
6b, R = H
6c, R = Si(CH$_3$)$_2$C(CH$_3$)$_3$

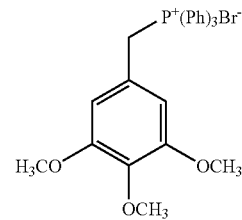

7

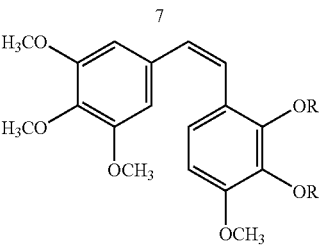

1, R = H
8, R = Si(CH$_3$)$_2$C(CH$_3$)$_3$

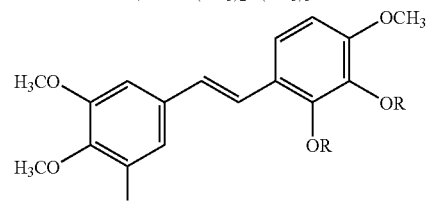

9a, R = Si(CH$_3$)$_2$C(CH$_3$)$_3$
9b, R = H

Once a practical scale-up synthesis of combretastatin A-1 (1) was in hand, phosphorylation with dibenzyl phosphite (Silverberg et al, 1996) was undertaken. Diphosphate 10 was obtained in high yield (97%). Removal of the benzyl protecting groups was carried out with in situ generation of trimethylsilyl iodide (TMSI) from reaction of sodium iodide and chlorotrimethylsilane (Jung & Lyster, 1977; Olah et al, 1979; Morita et al, 1978; Jung & Lyster, 1977; Ho & Olah, 1976; Salomon et al, 1993). Initially, TMSI-mediated cleavage afforded a large portion of the undesired trans-isomer, presumably from the electrophilic addition of iodine to form an iodonium ion and subsequent elimination to the trans-olefin (Hassner et al, 1970; Robertson et al, 1950; Zanger & Rabinowitz, 1975; Ayers et al, 1971; Skell & Pavlis, 1964). This problem was eventually circumvented through the use of new sodium iodide and the correct dilution of acetonitrile needed for the debenzylation. At higher concentrations and with the use of older sodium iodide the cleavage reaction produced a nearly 1:1 ratio of cis- to trans-isomers. More dilute solutions and new sodium iodide led almost exclusively to the desired cis- isomer (determined by NMR analysis).

The very successful benzyl ester cleavage reaction was preceeded by a number of other approaches and reagents that proved to be in general unsatisfactory. Unsuccessful debenzylation reactions applied to phosphate 10 included Raney nickel (W-2), ferric chloride, trimethylphenylthiosilane, chromium trioxide, catalytic transfer hydrogenolysis, mild hydrogenation (reaction times <10 min), DDQ, tripenylcarbenium, tin (IV) chloride, and lithium hydroxide. In most instances the above reaction conditions resulted in incomplete removal of the four benzyl groups and isomerization or reduction of the olefin group. This debenzylation step proved to be the most challenging synthetic obstacle in the synthesis of the desired prodrug, because of the very difficult isolation of the debenzylated diphosphate owing to its high solubility in water.

In order to try different protecting groups on the phosphate, several other methods of phosphorylation were attempted. These included the use of alkylamidophosphines, which have been shown to readily phosphorylate alcohols and phenols in high yield. For example, di-tert-butyloxy (N,N-diisopropylamido)phosphine, prepared from dichloro (N,N-diisopropylamido)phosphine and tert-butanol was allowed to react with diphenol 1 in the presence of 1H-tetrazole. After phosphorylating diphenol 1, subsequent in situ oxidation of the trivalent phosphorous to the pentavalent species with meta-chloroperoxybenzoic acid did not result in the desired phosphate. Perhaps this unpromising result arose from the steric crowding involved with four tert-butyl groups in the 2'- and 3'- positions, or from the oxidation step which may have effected the stilbene olefin. Interestingly, the use of dibenzyloxy(N,N-diisopropylamido)phosphine under the reaction conditions just described did afford phosphate 10 but only in 10% yield. Two other phosphorylation methods were attempted using di-tert-butyl phosphite with an in situ generation of the appropriate halide (Br, Cl), and N,N-diisopropylphosphorodiamidic chloride. Neither method led to the corresponding diphosphate analog of dibenzylphosphate 10. Diphosphorylation of 1 was also achieved in good yield with diethylcyano-phosphonate. However, this method proved to be problematic due to harsh conditions needed to remove an ethyl group.

The combretastatin A-1 prodrug 4 was synthesized via the acid-base reaction between the diphosphoric acid obtained from the sodium iodide/chlorotrimethylsilane mediated debenzylation of 10, and sodium methoxide in anhydrous methanol. Synthesis of the combretastatin B-1 prodrug (5) was carried out through the standard hydrogenation of diphosphate 10 followed by reaction with sodium methoxide in anhydrous methanol. Bibenzyl prodrug 5 showed reduced antineoplastic activity when compared to cis-stilbene prodrug 4, which is consistent with previous structure-activity relationship studies in the combretastatin series. As expected, both exhibited increased activity over their respective parent compounds. The relevant structures are shown in Figure 3, below.

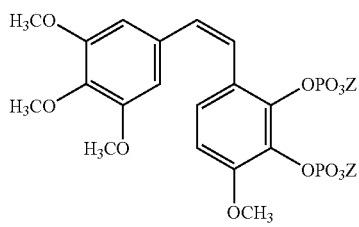

Figure 3

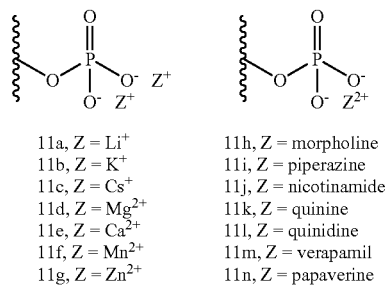

11a, Z = Li⁺
11b, Z = K⁺
11c, Z = Cs⁺
11d, Z = Mg²⁺
11e, Z = Ca²⁺
11f, Z = Mn²⁺
11g, Z = Zn²⁺

11h, Z = morpholine
11i, Z = piperazine
11j, Z = nicotinamide
11k, Z = quinine
11l, Z = quinidine
11m, Z = verapamil
11n, Z = papaverine Metal cation and ammonium salts of combretastatin A-1 2',3'-O-diphosphate Once an efficient method for the synthesis of prodrug 4 was in hand, various metal cation and ammonium salts of the phosphoric acid precursor were investigated. The cancer cell line and solubility behavior are summarized in Table I, below. Of the monovalent metal cation salts, the lithium (11a, 40 mg/mL), sodium (4, 120 mg/mL), potassium (11b, >90 mg/mL) and cesium (11c, >50 mg/mL) derivatives all showed good solubility in water while the divalent metal cation salts derived from magnesium, calcium, manganese, and zinc were progressively more insoluble owing perhaps to the formation of polymers. The low solubility of these divalent metal cations did not allow for a suitable HRMS, LRMS, $^1$H or $^{13}$C NMR to be acquired. Of the ammonium cation salts both the morpholine (11h, 50 mg/mL) and piperazine (11i, 34 mg/mL) showed excellent solubility characteristics. The remaining ammonium cation salts showed solubility effects related to the corresponding amine. The relevant structures of the amines and alkaloids used in Figure 3 are shown in Figure 4, below.

Figure 4

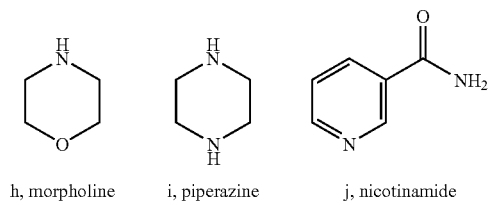

h, morpholine    i, piperazine    j, nicotinamide

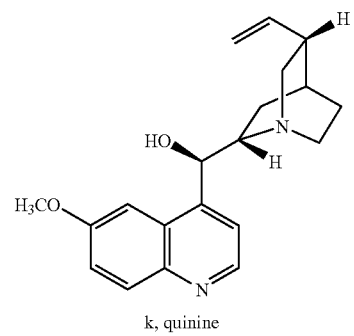

k, quinine

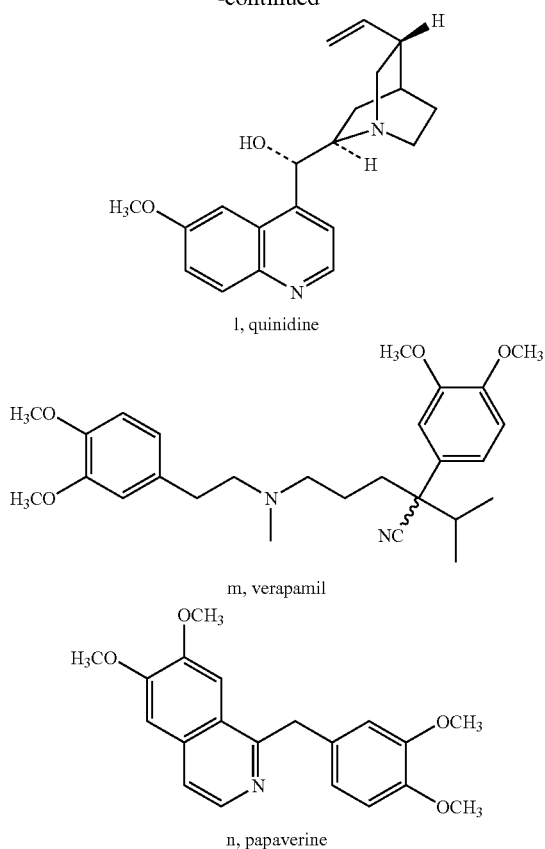

Amines and alkaloids used for the ammonium salts of combretastatin A-1 2',3'-O-diphosphate The biological activities of the metal cation prodrugs 11a–g mainly corresponded to the antimitotic properties of combretastatin A-1 (1) which appears to be among the most potent antagonists of colchicine binding to tubulin known, with nearly 99% inhibition of colchicine binding at equal concentrations (Pettit et al, 1987; Lin et al, 1988; Sackett, 1993), and thereby inhibiting tubulin polymerization. Various cations also play a role in the assembly or disassembly of microtubules. The relationship between site and affinity is largely unclear; divalent cations interact with tubulin in complex manners and are able to bind to them in both low- and high-affinity sites. The divalent cation magnesium has been shown to be essential for microtubule assembly and has been proposed to bind as a complex with a nucleotide at the exchangeable GTP [guanosine 5'-triphosphate ("GTP")] site. An adequate concentration of potassium cations is required to facilitate the microtubule formation and can be replaced by sodium ions. However, sodium ions begin to suppress the polymerization at lower concentrations as compared to potassium ions, suggesting that the factor involved is not the species of monovalent cations, but rather the ionic strength. Calcium ions inhibit the polymerization of tubulin and upon addition to preassembled microtubules cause their disassembly, while binding only weakly to tubulin at the magnesium site. A manganous cation can be substituted for the magnesium cation with normal microtubule assembly. Zinc cations have been shown to interfere with the lateral binding between the protofilaments of microtubules. Metal cation prodrugs 11a–g showed equal or less cytotoxicity versus the P388 and human tumor cell lines when compared to prodrug 4 (Table I).

TABLE I

Solubilities, Human Cancer Cell Line and Murine P-388 Lymphocytic Leukemia Inhibitory Activities of Combretastatins A-1, A-4, B-1 and Synthetic Modifications.

| Compound | Solubility[a] mg/ml | Leukemia P388 $ED_{50}$ μg/ml | Pancreas-a BXPC-3 | Ovarian OVCAR-3 |
|---|---|---|---|---|
| 1 | — | 0.251 | 4.4 | — |
| 2 | — | 1.7 | — | — |
| 3a | — | 0.0003 | 0.39 | <0.001 |
| 3c | 20 | 0.0004 | — | 0.023 |
| 4 | 120 | <0.0100 | 1.5 | 0.024 |
| 5 | >50 | 0.335 | >10 | 2.0 |
| 11a | 40 | <0.0100 | 0.33 | 0.028 |
| 11b | >90 | 0.0170 | 0.38 | 0.023 |
| 11c | >50 | 0.0365 | 0.31 | 0.024 |
| 11d | <1 | 0.0245 | 0.44 | 0.031 |
| 11e | <1 | 0.0102 | 0.28 | 0.024 |
| 11f | <1 | 0.715 | 4.7 | 0.044 |
| 11g | <1 | 0.0394 | 0.36 | 0.027 |
| 11h | 50 | 0.002 | 0.35 | 0.043 |
| 11i | 20 | 0.002 | 0.35 | 0.046 |
| 11j | 15 | 0.005 | 0.42 | 0.054 |
| 11k | <1 | 0.004 | 0.47 | 0.054 |
| 11l | <1 | 0.004 | 0.55 | 0.043 |
| 11m | <1 | 0.004 | 0.60 | 0.066 |
| 11n | <1 | 0.05 | 0.38 | 0.052 |

| Compound | Solubility[a] MG/ML | CNS SF-295 | Lung-NSC NCl-H460 $GI_{50}$ μg/ml | Colon KM20L2 | Prostate DU-I45 |
|---|---|---|---|---|---|
| 1 | — | — | 0.74 | — | 0.17 |
| 2 | — | — | — | — | — |
| 3a | — | <0.001 | 0.0006 | 0.061 | 0.0008 |
| 3c | 20 | 0.036 | 0.029 | 0.34 | — |
| 4 | 120 | 0.036 | 0.038 | 0.53 | 0.034 |
| 5 | >50 | 2.3 | 3.3 | >10 | 2.7 |
| 11a | 40 | 0.042 | 0.040 | 0.37 | 0.031 |
| 11b | >90 | 0.035 | 0.036 | 0.30 | 0.024 |
| 11c | >50 | 0.038 | 0.040 | 0.28 | 0.024 |
| 11d | <1 | 0.039 | 0.039 | 0.47 | 0.032 |
| 11e | <1 | 0.041 | 0.037 | 0.34 | 0.024 |
| 11f | <1 | 0.28 | 0.19 | 6.1 | 2.4 |
| 11g | <1 | 0.033 | 0.032 | 0.32 | 0.025 |
| 11h | 50 | 0.042 | 0.046 | 0.26 | 0.039 |
| 11i | 20 | 0.039 | 0.037 | 0.20 | 0.036 |
| 11j | 15 | 0.053 | 0.15 | 0.53 | 0.046 |
|  | <1 |  |  |  |  |
| 11k | <1 | 0.044 | 0.34 | 0.40 | 0.050 |
| 11l | <1 | 0.056 | 0.37 | 0.84 | 0.10 |
| 11m | <1 | 0.070 | 0.40 | 1.2 | 0.086 |
| 11n |  | 0.063 | 0.27 | 0.33 | 0.054 |

[a]Solubility values were obtained using 1 mL distilled water at 25° C.

The ammonium cation prodrugs 11h–n were synthesized in order to further evaluate aqueous solubility and to study their ability to reverse multidrug resistance through interference with the P-glycoprotein mechanism (11k–n) based on the amine in question. Morpholine, piperazine, and nicotinamide (NADH biosynthesis) have had relatively limited clinical use. On the other hand, cinchona alkaloids such as quinine and its sterioisomer quinidine have been used to extensively treat malaria. Similarly, verapamil has been clinically shown to be a calcium antagonist, and a potent cardiovascular agent with antianginal and antihypertensive properties, while also being used in the treatment of arrhythmias. Finally, papverine, isolated from opium, is best known for its muscle relaxing properties. Ammonium cation prodrug 11h–n all showed strong antineoplastic properties equal to or better than their metal cation counterparts (Table I).

2,3-Dihydroxy-4methoxy-benzaldehyde (6b)

An anhydrous dichloromethane (500 mL) solution of 2,3,4-trimethoxy-benzaldehyde (6a, 19.6 g, 100 mmol)

under argon at ambient temperature was stirred for 10 min and boron trichloride (100 mL, 100 mmol, 1 eq, 1.0 M soln in dichloromethane) was added. After 2 hours, the second equivalent of boron trichloride (100 mL, 100 mmol; 1 eq; 1.0 M solution in dichloromethane) was added. The dark reaction mixture was stirred for 24 hours, and then slowly poured into 10% sodium bicarbonate (aq) (40 g/360 mL). The resulting solution was acidified with concentrated hydrochloric acid to pH 1. The dichloromethane layer was separated, and the aqueous layer was extracted with ethyl acetate (4×100 mL) and dried. Evaporation of solvent in vacuo gave a brown oil, which was absorbed onto silica gel and subjected to flash column chromatography (50:50:1 hexane-ethyl acetate-acetic acid) to afford a yellow solid. Recrystallization from ethyl acetate-hexane gave yellow needles (12.4 g; 74%): m.p. 115–116° C. [lit. 116–117° C. (Pettit et al, 1987)]; $R_f$ 0.40 (1:1, hexane-ethyl acetate); EIMS m/z 168 (100%, M+), 125 (25%), 122 (40%), 79 (20%), 52 (20%). Anal. Calcd. for $C_8H_8O_4$: C, 57.14; H, 4.80. Found: C, 57.23; H. 4.79.

2,3-Bis[tert-butyldimethylsiloxy]-4-methoxy-benzaldehyde (6c)

Preparation of silyl ether 6c was repeated essentially as originally described (Pettit et al, 1987) from diphenol 6b (12.4 g) except for modification of its purification procedure. Evaporation (under reduced pressure) of the ethyl acetate used for extraction yielded a brown oil, which was absorbed onto silica gel and subjected to flash column chromatography (15:1 hexane-ethyl acetate). The light yellow oily product was crystallized from methanol to afford the title compound as a colorless solid (25.5 g; 87% yield): m.p. 74–75° C. [lit. 74.5–76° C. (Pettit et al, 1987)]; $R_f$ 0.80 (15:1, hexane-ethyl acetate); EIMS m/z 396 (2%, M+), 381 (10%), 339 (100%), 267 (15%), 73 (85%); $^1$H NMR (300 MHz, CDCl$_3$) δ 0.14 (12H, s, 4×SiCH$_3$), 0.99 (9H, s, 3×CH$_3$), 1.05 (9H, s, 3×CH$_3$), 3.84 (3H, s, OCH$_3$), 6.63 (1H, d, J=8.7 Hz, H-5), 7.49 (1H, d, J=8.1 Hz, H-6), 10.23 (1H, s, CHO). Anal. Calcd. for $C_{30}H_{36}O_4Si_2$: C, 60.56; H, 9.15. Found: C, 60.53; H, 9.38.

3,4,5-Trimethoxybenzyltriphenylphosphonium Bromide (7)

Several modifications of the prior synthesis of this phosphonium bromide (7) were employed here. The reaction mixture prepared from triphenylphosphine (24.1 g, 92.0 mmol, 1.1 eq) and 3,4,5-trimethoxybenzyl bromide (21.3 g, 80.0 mmol) in toluene (200 mL) was heated at reflux for 6 hours and stirred for 18 hours at room temperature. Evaporation of the solvent in vacuo resulted in a crude solid, which was recrystallized from ethyl acetate-hexane to afford colorless crystals (39.0 g, 93%): m.p. 219–220° C. [lit. 222–223° C. (Pettit et al, 1987)]; $R_f$ 0.00 (1:1, hexane-ethyl acetate); TOFMS m/z 443 [M-Br]+; IR (film) $v_{max}$ 1590, 1508, 1465, 1435, 1332, 1238, 1126, 997, 974, 873 cm$^{-1}$; $^1$H NMR (300 MHz, CDCl$_3$) δ 3.51 (6H, s, 2×OCH$_3$), 3.77 (3H, s, OCH$_3$), 5.40 (2H, d, J=14 Hz, Ph-CH$_2$), 6.48 (2H, bs, H-2, H-6), 7.70 (15H, m, P(Ph)$_3$). Anal. Calcd. for $C_{28}H_{28}O_3PBr\cdot\frac{1}{2}H_2O$: C, 63.17; H, 5.49. Found: C, 62.97; H, 5.63.

2';3'-Di[tert-butldimethylsily-oxy]-(Z) and (E)-combretastatin A-1(8 and 9a)

Except for the purification procedure, the earlier synthesis was repeated using 26.5 g of aldehyde 6c. Evaporation (in vacuo) of the ethyl acetate solution used for extraction afforded a crude brown oil. Subjection to silica gel flash column chromatography (2×; 9:1 hexane-ethyl acetate followed by 60:1:1 hexane-ethyl acetate-triethylamine) led to both the pure (Z)- and (E)-isomers: cis-Silyl ether 8 (16.1 g, 43% yield, colorless crystals) from ethanol: m.p. 130–131° C. [lit. 117–118° C. (Pettit et al, 1987)]; $R_f$ 0.44 (9:1, hexane-ethyl acetate); EIMS m/z 560 (55%, M+), 503 (20%), 488 (40%), 431 (20%), 73 (100%); IR(film) $v_{max}$ 2955, 2858, 1579, 1498, 1462, 1313, 1246, 1128, 1105, 842 cm$^{-1}$; $^1$H NMR (300 MHz, CDCl$_3$) δ 0.11 (6H, s, SiCH$_3$×2), 0.19 (6H, s, SiCH$_3$×2), 1.00 (9H, s, 3×CH$_3$), 1.04 (9H, s, 3×CH$_3$), 3.68 (6H, s, 2×OCH$_3$), 3.74 (3H, s, OCH$_3$), 3.84 (3H, s, OCH$_3$), 6.36 (1H, d, J=12 Hz, —CH═CH—), 6.36 (1H, d, J=9.3 Hz, H-5'), 6.59 (1H, d, J=12 Hz, —CH═CH—), 6.62 (2H, s, H-2, H-6), 6.89 (1H, d, J=8.1 Hz, H-6'). Anal. Calcd. for $C_{30}H_{48}O_6Si_2$: C, 64.24; H, 8.62. Found: C, 64.30; H, 8.83. trans-Silyl ether 9a (5.0 g, 13% yield) was obtained as a colorless fluffy solid from ethanol: m.p. 139–140° C. [lit. 139–140° C. (Pettit et al, 1987)]; $R_f$ 0.40 (9:1, hexane-ethyl acetate); EIMS m/z 560 (55%, M+), 503 (10%), 488 (25%), 431 (15%), 73 (100%); IR (film) $v_{max}$ 1581, 1494, 1460, 1442, 1309, 1240, 1128, 1101, 837, 783 cm$^{-1}$; $^1$H NMR(300 MHz, CDCl$_3$) δ 0.11 (6H, s, SiCH$_3$×2), 0.13 (6H, s, SiCH$_3$×2), 1.00 (9H, s, 3×CH$_3$), 1.09 (9H, s, 3×CH$_3$), 3.79 (3H, s, OCH$_3$), 3.86 (3H, s, OCH$_3$), 3.88 (6H, s, 2×OCH$_3$), 6.56 (1H, d, J=8.7 Hz, H-5'), 6.72 (2H, s, H-2, H-6), 6.80 (1H, d, J=16 Hz, —CH═CH—), 7.20 (1H d, J=9.0 Hz, H-6'), 7.31 (1H, d, J=16 Hz, —CH═CH—). Anal. Calcd. for $C_{30}H_{48}O_6Si_2$: C, 64.24; H, 8.62. Found: C, 64.19; H, 8.94.

Photochemical Isomerization of (Z)-stilbene 8 to (E)-stilbene 9a

A solution of 8 (10.6 g; 18.9 mmol) in chloroform was irradiated directly from below with long-wave length (366 nm) UV for 5 hours. The ultraviolet source was a UV lamp used for visualizing TLC plates equipped with both short-wave (254 nm) and long-wave (366 nm) lamps. The product was separated by silica gel flash column chromatography (9:1, hexane-ethyl acetate). The resulting colorless solid was recrystallized from ethyl alcohol to yield (8.6 g; 81%) the trans-stilbene 9a as a colorless fluffy solid. The product was identical (spectroscopically) to the specimen synthesized in the preceding experiment.

Combretastatin A-1 (1)

Method A.

Potassium fluoride (0.22 g, 3.79 mmol, 4 eq) was added to a solution of bis-silyl ether 8 (0.52 g, 0.929 mmol) dissolved in DMF (6 mL under argon at ambient temperature). The mixture was stirred for 5 min and a catalytic amount of 48% aq. HBr (11 μL, 0.20 mmol 0.2 eq) was added. After 18 hours of stirring, the resulting mixture was poured over ice-cold 6N hydrochloric acid (aq). Following extraction of the mixture with ethyl acetate (3×25 mL), the combined extract was washed with saturated sodium chloride (aq) and dried. Removal of solvent in vacuo gave a light brown oil, which was separated by column chromatography (50:50:1 hexane-ethyl acetate-acetic acid) to afford a clear oil. Crystallization from ethyl acetate-hexane yielded colorless crystals (0.20 g, 68% yield): m.p. 117–118° C. [lit. 114–115° C. (Pettit et al, 1987)]; $R_f$ 0.67 (50:50:1 hexane-ethyl acetate-acetic acid); EIMS m/z 332 (100%, M+), 317 (90%), 257 (7%), 166 (5%), 115 (8%); IR (film) $v_{max}$ 3443, 1624, 1581, 1504, 1462, 1329, 1238, 1124, 1093, 1001 cm$^{-1}$; $^1$H NMR (300 MHz, CDCl$_3$) δ 3.67 (6H, s, 2×OCH$_3$), 3.83 (3H, s, OCH$_3$), 3.86 (3H, s, OCH$_3$), 5.38 (2H, s, 2×OH, 2',3'D$_2$O exchanged), 6.39 (1H, d, J=9.0 Hz, H-5'), 6.53 (2H, s, H-2, H-6), 6.53 (1H, d, J=12 Hz, —CH═CH—, 6.60 (1H, d, J=12 Hz, —CH═CH—, 6.77 (1H, d, J=8.7 Hz, H-6'); $^{13}$C NMR (125 MHz, CDCl$_3$) δ 152.71, 146.29, 141.65, 137.16, 132.54, 132.46, 130.11, 124.02, 120.27, 117.77, 105.88, 102.85, 60.79, 56.10, 55.77. Anal. Calcd. for $C_{18}H_{20}O_6$: C, 65.05; H 6.06. Found: C, 65.04; H, 6.28.

Method B.

To a solution of bis-silyl ether 8 (2.0 g, 3.53 mmol) in anhydrous THF (10 mL) was added tetrabutylammonium fluoride (1 min TBF; 7.8 mL, 7.80 mmol, 2.2 eq). The mixture was stirred for 25 min. Ice-cold 6N hydrochloric acid (aq) was added, and the mixture was extracted with ethyl acetate (4×25 mL). The combined organic extracts were washed with saturated sodium chloride (aq) (50 mL) and dried. Removal of the solvent under reduced pressure yielded a dark brown oil (quantitative yield), which was dried in high vacuum and then immediately phosphorylated to provide bis phosphate ester 10.

2',3'-Dihydroxy-3,4,4',5-tetramethoxy-(E)-stilbene (9b, Trans-combretastatin A-1)

The same desilylation procedure was performed on silyl ether 9b described in Method B above for the desilylation of 8 to combretastatin A-1(1). trans-Stilbene 9b was isolated following column chromatography (50:50:1 hexane-ethyl acetate-acetic acid) as a clear oil that crystallized from ethyl acetate-hexane: colorless crystals (1.0 g, 70% yield); m.p. 48–50° C.; $R_f$ 0.65 (50:50:1 hexane-ethyl acetate-acetic acid); TOFMS m/z 332 [M]$^+$; IR (film) $v_{max}$ 3408, 2937, 1622, 1581, 1510, 1464, 1290, 1238, 1126, 1003 cm$^{-1}$; $^1$H NMR(300 MHz, CDCl$_3$) δ 3.86 (3H, s, OCH$_3$), 3.89 (3H, s, OCH$_3$), 3.91 (6 H, s, 2×OCH$_3$), 6.50 (1H, d, J=8.7 Hz, H-5'), 6.74 (2H, s, H-2, H-6), 7.05 (1H, d, J=16 Hz, —CH═CH—), 7.05 (1H, d, J=8.7 Hz, H-6'), 7.23 (1H, d, J=16 Hz, —C═C—). $^{13}$C NMR (125 MHz, CDCl$_3$) δ 153.34, 146.24, 142.15, 133.95, 132.32, 127.84, 122.82, 118.37, 117.72, 103.46, 103.09, 60.93, 56.11. Anal. Calcd. for $C_{18}H_{20}O_6$: C, 65.05; H, 6.06. Found: C, 64.53; H, 6.41.

2',3'-O-Di-[Bis-benzylphosphoryl]Combretastatin A-1(10)

To a solution of diphenol 1 (5.6 g; 17.0 mmol) in acetonitrile (100 mL cooled to −20° C.) was added carbon tetrachloride (16 m/L, 170 mmol, 10 eq). The resulting solution was stirred for 10 min prior to adding DIPEA (12 mL, 71 Mmol, 4.2 eq via syringe) and DMAP (0.42 g, 3.40 mmol, 0.2 eq). Approximately 1 min later, the slow (dropwise) addition of dibenzyl phosphite (1 mL, 49 mmol; 2.9 eq) was begun at such a rate that the stirred reaction mixture temperature was kept below −20° C. After 45 min, 0.5M KH$_2$PO$_4$ (aq) was added and the mixture allowed to warm to room temperature. An ethyl acetate extract (4×50 mL) was washed with saturated sodium chloride (aq), followed by water, and dried. Removal of solvent in vacuo yielded a yellow oil that was further separated by flash column chromatography (3:2 hexane-ethyl acetate) to afford 14 g (97%) of a golden oil: $R_f$ 0.31 (1:1, hexane-ethyl acetate); EIMS m/z 852 (20%, M$^+$), 762 (5%), 484 (40%), 277 (10%), 91 (100%); IR (film) $v_{max}$ 2941, 2839, 1579, 1502, 1454, 1282, 1126, 1012, 966, 738 cm$^{-1}$; $^1$H NMR (300 MHz, CDCl$_3$) δ 3.62 (6H, s, 2×OCH$_3$), 3.77 (3H, s, OCH$_3$), 3.80 (3H, s, OCH$_3$), 5.08 (4H, m, 2×CH$_2$-Ph), 5.17 (4H, m, 2×CH$_2$-Ph), 6.46 (2H, s, H-2, H-6), 6.51 (1H, d, J=12 Hz, —CH═CH—), 6.64 (1H, d, J=12 Hz, —CH═CH—), 6.67 (1H, d, J=8.7 Hz, H-5'), 7.00 (1H, d, J=8.1 Hz, H-6'), 7.25 (20H, m, 4×C$_6$H$_5$; $^{13}$C NMR (125 Mz, CDCl$_3$) δ 152.60, 151.36, 141.13, 137.04, 135.71, 135.65, 135.46, 135.40, 132.81, 131.87, 131.49, 128.25, 128.14, 127.71. 127.57, 126.67, 124.37, 124.16, 109.16, 106.00, 69.76, 69.72, 69.55, 69.51, 60.60, 56.23, 55.72; $^{31}$P NMR (202 MHz, CDCl$_3$) δ −4.81 (J=2.6 Hz), −4.92 (J=2.8 Hz). Anal. Calcd. for $C_{46}H_{46}O_{12}P_2$: C, 64.79; H. 5.44. Found: C, 64.65; H 5.53.

2',3'-O-Di[Bis-benzylphosphoryl]-Combretastatin A-1 (10)

1H-Tetrazole (70 mg; 0.96 mmol; 6.5 eq) was added in one portion to a stirred solution of diphenol 1 (50 mg; 0.15 mmol) and dibenzyl N,N-diisopropylphosphoramidite (0.12 g; 0.34 mmol; 2.2 eq) in dry tetrahydrofuran (1 mL) and stirred for 15 min at room temperature. The mixture was then cooled to −50° C., and a solution of 85% meta-chloroperoxybenzoic acid in dichloromethane was rapidly added such that the reaction temperature was kept below 0° C. After stirring for 5 min at room temperature, 10% aqueous sodium thiosulfate was added and the mixture stirred further for 10 min. The resulting mixture was then extracted with ethyl acetate (4×10 mL), washed with 10% aqueous sodium thiosulfate, 0.5 M aqueous sodium hydroxide, and dried. Evaporation of the solvent under reduced pressure gave a yellow oil that was then subjected to flash column chromatography (3:2, hexane-ethyl acetate) to afford a clear oil (15 mg; 10%) spectroscopically identical to the product generated from the dibenzyl phosphite phosphorylation above.

2',3'-O-Di[Bis-ethylphosphoryl]-Combretastatin-A1

Combretastatin A-1 (0.10 g; 0.30 mmol) was dissolved in dry dichloromethane (5 mL). The solution was then cooled to 0° C. and then diethyl cyanophosphonate (0.10 mL; 0.66 mmol; 2.2 eq). followed by triethylamine (0.17 mL; 1.2 mmol; 4 eq) were added. After stirring at 0° C. for 2.5 hours the mixture was extracted with dichloromethane (4×20 mL), the combined organic extract washed with water, and dried. Evaporation of the solvent in vacuo yielded a light yellow oil which was purified by flash column chromatography (3:2, ethyl acetate-hexane) to afford a clear oil (0.14 g; 75%): $R_f$ 0.38 (3:2, ethyl acetate-hexane); EIMS m/z 604 (100%, M$^+$), 468 (10%), 369 (5%), 206 (5%), 45 (20%); IR (film) $v_{max}$ 2984, 1608, 1579, 1504, 1454, 1419, 1327, 1273, 1240, 1126 cm$^{-1}$; $^1$H NMR (300 MHz, CDCl$_3$) δ 1.31–1.39 (12 H, m, 4×OCH$_2$O<u>CH</u>$_3$), 3.66 (6H, s, 2×OCH$_3$), 3.81 (3H, s, OCH$_3$), 3.85 (3H, s, OCH$_3$), 4.2–4.34 (8H, m, 4×O<u>CH</u>$_2$OCH$_3$), 6.48 (2H, s, H-2, H-6), 6.56 (1H, d, J=12 Hz, —CH═CH—), 6.65 (1H, d, J=7.8 Hz, H-5'), 6.66 (1H, d, J=12 Hz, —CH═CH—), 6.97 (1H, d, J=8.7 Hz, H-6'). Anal. Calcd. For $C_{26}H_{38}O_{12}P_2$: C, 51.66; H, 6.34. Found: C, 51.66; H, 6.46.

Sodium Combretastatin A-1 2',3'-O-diphosphate (4)

To a solution of phosphate 10 (3.2 g, 3.69 mmol) in acetonitrile (40 mL) under argon was added sodium iodide (2.2 g, 14.8 mmol, 4 eq). Before dropwise addition of chlorotrimethylsilane (1.9 mL, 14.9 mmol, 4 eq), the mixture was stirred for 2 min. and 30 min later the reaction was terminated with 1% aq sodium thiosulfate (4 mL). Removal of the acetonitrile in vaco afforded a crude mixture, which was dissolved in water-dichloromethane and washed with water (4×10 mL). Concentration (facilitated by toluene azeotrope) of the aqueous layer resulted in isolation of the crude phosporic acid intermediate which was subjected to drying in high vacuum (1 hour) and then dissolved in dry methanol (10 mL under argon). Next sodium methoxide (0.80 g, 14.8 mmol, 4 eq) was added. The mixture was allowed to stir (6 hours) and additional methanol was added to effect dissolution. After filtration of the solution, concentration of the methanol in vacuo led to an off-white solid, which was reprecipitated from water-ethanol to yield a colorless powder (1.7 g, 81% yield): m.p. 168–170° C. (dec.); UV λmax (H$_2$O) 298 nm (log ϵ, 4.16); IR (KBr)$v_{max}$ 3364, 1647, 1579, 1506, 1446, 1315, 1238, 1126, 1093,991 cm$^{-1}$; $^1$H NMR (300 MHz, D$_2$O) δ 3.63 (6H, s, 2×OCH$_3$), 3.66 (6H, s, 2×OCH$_3$), 6.41 (1H, d, J=12 Hz, —CH═CH—), 6.43 (1H, d, J=8.7 Hz, H-5'), 6.70 (2H, s, H-2, H-6), 6.81 (1H, d, J=8.7 Hz, H-6'), 6.94 (1H, d, J=12 Hz, —C═C—); $^{13}$C NMR (75 MHz, CD$_3$OD) δ 153.56, 153.12, 136.73, 135.31, 129.12, 128.50, 124.88, 124.36, 107.71, 61.89, 57.16, 56.82; $^-$P NMR (202 MHz, D$_2$O) δ

2.07, 1.78. HRFAB MS m/z (peak height) 580.9958 (100%, M+H), Calcd. for $C_{18}H_{19}O_{12}Na_4P_2$: 580.9942.

Sodium Combretastatin B-1 2',3'-O-Diphosphate (5)

To a solution of phosphate 10 (1.1 g, 1.28 mmol) in methanol (5 mL in a hydrogenation flask), was added 10%/o Pd/C (1.1 g, 1 wt. eq). The mixture was hydrogenated for 24 hours at 35 psi. Filtration of the solution through celite and subsequent evaporation of solvent in vacuo afforded a light brown oil. Anhydrous methanol (5 mL) was added to the crude diphosphate followed by sodium methoxide (0.28 g, 5.13 mmol, 4 eq). The mixture was stirred for 6 hours, at which point additional methanol was added until the product dissolved. Filtration of the methanol solution and subsequent concentration in vacuo afforded a colorless solid, which was reprecipitated from methanol-acetone to yield a colorless powder (0.55 g, 74% yield): m.p. 170–172° C. (dec.); UV $\lambda_{max}$. (H$_2$O) 269 nm (log ε, 3.24); IR (KBr) $v_{max}$ 3385, 1589, 1496, 1458, 1236, 1186, 1124, 1087, 995, 559, cm$^{-1}$; $^1$H NMR (300 MHz, D$_2$O) δ 2.75 (2H, t, J=7.2 Hz, CH$_2$), 2.94 (2H, t, J=8.1 Hz, CH$_2$), 3.62 (3H, s, OCH$_3$), 3.67 (3H, s, OCH$_3$), 3.73 (6H, s, 2×OCH$_3$), 6.65 (1H, d, J=8.1 Hz, H-5'), 6.61 (2H, s, H-2, H-6), 6.66 (1H, d, J=9.0 Hz; H-6'), $^{13}$C NMR (100 MHz, CDCl$_3$) δ 153.13, 152.20, 146.31, 141.01, 137.13, 135.55, 129.30, 124.00, 108.05, 107.28, 61.85, 57.08, 56.84, 36.88, 32.50; $^{31}$P NMR (162 MHz, D$_2$O) δ 1.74, 1.36. HRFAB MS m/z (peak height) 583.0097 (100%, M+H), Calcd. for $C_{18}H_{21}O_{12}Na_4P_2$: 583.0099.

General Procedure for Synthesis of the Combretastatin A-1 Phosphate Prodrugs

Method A.

Each of the metal cation-containing salts was obtained by this procedure as outlined directly below for preparing the tetralithium salt 11a.

Lithium Combretastatin A-1 2',3'-O-diphosphate (11a)

To a solution of phosphate 10 (0.42 g, 0.488 mmol) in acetonitrile (5 mL, under argon) was added sodium iodide (0.29 g, 1.95 mmol, 4 eq). The mixture was stirred for 2 min, and chlorotrimethylsilane (0.25 mL, 1.95 mmol, 4 eq) was added (dropwise). After stirring for 30 min, the reaction was stopped with 1% aq sodium thiosulfate (2 mL). Removal of the acetonitrile in vacuo afforded a residue that was treated with 1.0 M lithium hydroxide dissolved in methanol (2.1 mL, 2.1 mmol, 4.1 eq) for 6 hours. The product was reprecipitated from water-ethanol to yield an off white powder (0.23 g, 92%): m.p. 138–140° C. (dec.); IR (KBr) $v_{max}$ 3311, 1579, 1508, 1442, 1303, 1240, 1167, 1132, 1012, 533, cm$^{-1}$; $^1$H NMR (300 MHz, D$_2$O) δ 3.62 (6H, s, 2×OCH$_3$), 3.65 (6H s, 2×OCH$_3$), 6.42 (1H, d, J=13 Hz, —CH═CH—), 6.43 (1H, d, J=7.2 Hz, H-5'), 6.69 (2H, s, H-2, H-6), 6.80 (1H, d, J=8.7 Hz, H-6'), 6.91 (1H, d, J=12 Hz, —CH═CH—); LRFAB MS: m/z (peak height) 509 [(anion+3 Li)$^-$, 50%], 503 [(anion+2 Li+H)$^-$, 100%], 497 [(anion+Li+2H)$^-$, 80%].

Potassium Combretastatin A-1 2',3'-O-diphosphate (11b)

The potassium salt reprecipitated from water-ethanol as a colorless powder (0.27 g; 83%): m.p. 113–115° C. (dec.); IR (KBr) $v_{max}$ 3383, 1653, 1579, 1506, 1456, 1419, 1126, 1089, 989, 545 cm$^{-1}$; $^1$H NMR (300 MHz, D$_2$O) δ 3.62 (6H, s, 2×OCH$_3$), 3.65 (3H, s, OCH$_3$) 3.66(3H s, OCH$_3$), 6.42 (1H, d, J=12 Hz, —CH═CH—), 6.44 (1H, d, J=8.7 Hz, H-5'), 6.68 (2H, s, H-2, H-6), 6.81 (1H, d, J=8.1 Hz, H-6'), 6.91 (1H, d, J=12 Hz, —CH═CH—).

Cesium Combretastatin A-1 2',3'-O-diphosphate (11c)

Reprecipitation from water-ethanol yielded a colorless powder (0.22 g) (36%) m.p. 142–144° C. (dec.);IR (KBr) $v_{max}$ 3385, 1577,1506, 1456, 1419, 1238, 1126, 1089, 985, 545 cm$^{-1}$; $^1$H NMR (300 MHz, D$_2$O) δ 3.61 (6H, s, 2×OCH$_3$), 3.65 (3H, s, OCH$_3$), 3.66 (3H, s, OCH$_3$), 6.43 (1H, d, J=13 Hz, —CH═CH—), 6.45 (1H, d, J=8.7 Hz, H-5'), 6.67 (2H, s, H-2,H-6), 6.80 (1H, d, J=8.7 Hz, H-6'), 6.89 (1H, d, J=13 Hz, —CH═CH—).

Magnesium Combretastatin A-1 2',3'-O-diphosphate (11d)

The precipitate from the reaction was filtered and washed with water to afford a cream colored powder (0.20 g; 80%) m.p. 150–152° C. (dec.); IR (KBr) $v_{max}$ 3421, 1635, 1579, 1498, 1446, 1236, 1126, 1099, 1006, 547 cm$^{-1}$.

Calcium Combretastatin A-1 2',3'-O-diphosphate (11e)

The precipitate from the reaction was filtered and washed with water to afford a cream-colored powder (0.24 g; 70%): m.p. 163–165° C. (dec.); IR (KBr) $v_{max}$ 3445, 1577, 1506, 1456, 1238, 1126, 1097, 1004, 837, 526 cm$^{-1}$. LRFAB MS (peak height) 529 [(anion+Ca+H)$^-$, 10%].

Manganese Combretastatin A-1 2', 3'-O-diphosphate (11f)

The precipitate from the reaction was filtered and washed with water to afford a tan powder (0.12 g; 55%) m.p. 135–137° C. (dec.); IR (KBr) $v_{max}$ 3447, 1575, 1506, 1456, 1317, 1126, 1095, 1004, 667, 518 cm$^{-1}$. LRFAB MS m/z (peak height) 543 [(anion+Mn+H)$^-$, 15%].

Dizinc Combretastatin A-1 2',3'-O-diphosphate (11g)

The precipitate from the reaction was filtered and washed with water to afford a colorless powder (0.28 g; 86%): m.p. 243–245° C. (dec.); IR (KBr) $v_{max}$ 3441, 1579, 1506, 1456, 1421, 1315, 1238, 1163, 1126, 1097, cm$^{-1}$.

Method B.

Each of the ammonium cation salts (11h–n) of combretastatin A-1 phosphate was prepared by this general procedure. The same method as described for prodrugs 11a–g was used, except that the appropriate amine or alkaloid (4 eq.) was added to the phosphoric acid to yield prodrugs 11h–n. All reaction mixtures were stirred for 8 hours and recrystallization/reprecipitation was performed with methanol-ether unless otherwise stated. These ammonium cation salts were investigated by HRFAB MS and the results were erratic. Presumably, this was due to various anion cation combinations and other types of associations. However, in each case it was clear that a salt of the same composition was obtained that was suitable for our purposes.

Morpholine Combretastatin A-1 2',3'-O-diphosphate (11h)

Reprecipitation yielded a colorless solid (0.26 g): m.p. 168–170° C. (dec.); IR (KBr) $v_{max}$ 3402, 3014, 2868, 2470, 1579, 1498, 1450, 1313, 1126, 1103 cm$^{-1}$; $^1$H NMR(300 MHz, D$_2$O) δ 3.12 (8H,t, J=4.5 Hz, CH$_2$OCH$_2$×2), 3.61 (6H, s, 2×OCH$_3$), 3.66 (3H, s, OCH$_3$), 3.72 (3H, s, OCH$_3$), 3.81 (8H, t, J=4.8 Hz, CH$_2$NCH$_2$×2), 6.51 (1H, d, J=12 Hz, —CH═CH—), 6.55 (1H, d, J=8.7 Hz, H-5'), 6.61 (2H, s, H-2, H-6), 6.74 (1H, d, J=12 Hz, —CH═CH), 6.81 (1H, d, J=8.7 Hz, H-6').

Piperazine Combretastatin in A-1 2',3'-O-diphosphate (11i).

Reprecipitation from ethanol-water yielded a colorless solid (0.34 g): m.p. 139–141° C. (dec.); IR (KBr) $v_{max}$ 3406, 3005, 2839, 1579, 1498, 1446, 1126, 1093, 989, 949 cm$^{-1}$; $^1$H NMR (300 MHz, D$_2$O) δ 3.05 (6H, brs, —CH$_2$—), 3.59 (6H, s, 2×OCH$_3$), 3.65 (3H, s, OCH$_3$), 3.71 (3H, s, OCH$_3$), 6.51 (1H, d, J=12 Hz, —CH═CH—), 6.54 (1H, d, J=8.4 Hz, H-5'), 6.60 (2 H, s, H-2, H-6), 6.72 (1H, d, J=12 Hz, —CH═CH—), 6.79 (1H, d, J=8.7 Hz, H-6').

Nicotinamide Combretastatin A-1 2',3'-O-diphosphate (11j).

Reprecipitation yielded a cream-colored solid (0.46 g): m.p. 148–150° C. (dec.); IR (KBr) $v_{max}$ 3350, 3090, 2937, 2837, 1689, 1577, 1498, 1448, 1124, 1097 cm$^{-1}$; $^1$H NMR (300 MHz, D$_2$O) δ 3.54 (6H, s, 2×OCH$_3$), 3.60 (3H, s, OCH$_3$), 3.72 (3H, s, OCH$_3$), 6.46 (2H, s, H-2, H-6), 6.47 (1H, d, J=12 Hz, —CH═CH—), 6.57 (1H, d, J=8.7 Hz, H-5'), 6.61 (1H d, J=11 Hz, —CH═CH—), 6.75 (1H, d, J=8.7 Hz, H-6'), 8.02 (1H, dd, J=8.4 Hz), 8.77 (1H, d, J=8.1 Hz), 8.82 (1H, d, J=8.4 Hz), 9.05 (1H, s).

Quinine Combretastatin A-1 2',3'-O-dephosphate (11k).

Reprecipitation yielded a cream-colored solid (0.48 g): m.p. 144–146° C.(dec.); $[\alpha]D^{25}$ −35° (c=1.12, MeOH); IR (KBr) $v_{max}$ 3383, 2941, 1620, 1579, 1504, 1446, 1240, 1126, 1091, 987 cm$^{-1}$; $^1$H NMR (300 MHz, D$_2$O) δ 1.25 (2H, brs), 1.69 (3H, brs), 1.87 (1H, brs), 2.49 (2H, brs), 2.93 (2H, brs), 3.20 (1H, brs), 3.50 (6H, s, 2×OCH$_3$), 3.57 (3H, s, OCH$_3$), 3.62 (3H, s, OCH$_3$), 3.80 (3H, s, OCH$_3$), 4.74–5.10 (2H, m) 5.48–5.60 (1H, m), 5.81 (1H, brs), 6.32 (1H, d, J=12 Hz, —CH═CH—), 6.37 (1H, d, J=9.0 Hz, H-5'), 6.43 (2H, s, H-2, H-6), 6.67 (1H, d, J=8.7 Hz, H-6'), 6.70 (1H, d, J=12 Hz, —CH═CH—), 7.14 (1H, d, J=11 Hz), 7.27 (1H, d, J=7.5 Hz), 7.49 (1H, d, J=4.5 Hz), 7.78 (1H, d, J=10 Hz), 8.51 (1H, d, J=4.2 Hz).

Quinidine Combretastatin A-1 2',3'-O-diphosphate (11l).

Reprecipitation yielded a light cream-colored solid (0.57) g: m.p. 158–160° C. (dec.): $[\alpha]D^{25}$+88° (c=1.05, MeOH); IR (KBr) $v_{max}$ 3385, 3084, 2943, 2359, 1622, 1510, 1454, 1244, 1126, 1093 cm$^{-1}$; $^1$H NMR (300 MHz, CD$_3$OD) δ 0.94 (2H, m), 1.54–1.67 (3H, m), 1.75 (1H, brs), 2.14–2.21 (2H, m), 2.40 (2H, m), 2.95–3.16 (1H, m), 3.49 (6H, s, 2×OCH$_3$), 3.56 (3H, s, OCH$_3$), 3.58 (3H, s, OCH$_3$), 3.81 (3H, s, OCH$_3$), 4.99–5.07 (2H, m), 5.88–5.99 (1H, m), 6.04 (1H, brs), 6.23 (1H, d, J=13 Hz, —CH═CH—), 6.35 (1H, d, J=8.4 Hz, H-5'), 6.36 (2H, s, -2, H-6), 6.68 (1H, d, J=8.4 H. H-6'), 6.76 (1H, d, J=13 Hz, —CH═CH—), 7.21–7.26 (2H, m), 7.58 (1H, d, J=4.8 Hz), 7.78 (1H, d, J=8.7 Hz), 8.52(1H, d, J=4.2 Hz).

Verapamil Combretastatin A-1 2',3'-O-diphosphate (11m).

Reprecipitation yielded a light cream colored solid (0.39 g): m.p. 160–162° C.; IR (KBr) $v_{max}$ 3427, 2960, 2362, 1577, 1498, 1452, 1217, 1126, 1060, 945 cm$^{-1}$; $^1$H NMR (300 MHz, D$_2$O/CD$_3$OD) δ 0.58 (3H, d, J=6.6 Hz, (CH$_3$)$_2$CH), 1.00 (3H, d, J=6.6 Hz, (CH$_3$)$_2$CH),. 1.42–2.16 (5H, m, CH$_2$CH$_2$CH$_2$N and (CH$_3$)$_2$CH), 2.65 (3H, s, NCH$_3$), 2.79–3.02 (6H, m, CH$_2$ NCH$_2$C$_2$PH), 3.51 (6H, s, 2×OCH$_3$), 3.58 (3H, s, OCH$_3$), 3.65 (3H, s, OCH$_3$), 3.66 (9H, s, 3×OCH$_3$), 3.67 (3H, s, OCH$_3$), 6.45 (1H, d, J=12 Hz, —CH═CH—), 6.49 (2H, s, H-2, H-6), 6.53 (1H, d, J=8.7 Hz, H-5'), 6.65 (1H, d, J=12 Hz, —CH═CH—), 6.67–6.86 (6H, m, Aryl H's), 6.72 (1H, d, J=8.7 Hz, H-6').

Papaverine Combretastatin A-1 2',3'-O-diphosphate (11n).

Reprecipitation yielded a cream colored solid (0.65 g): m.p. 149–151° C. (dec.); IR (KBr) $v_{max}$ 3447, 2937, 2837, 2449, 1605, 1510, 1452, 1298, 1234, 1126 cm$^{-1}$;$^1$H NMR (300 MHz, D$_2$O/CD$_3$OD) δ 3.44 (6H, s, 2×OCH$_3$), 3.54 (3H, s, OCH$_3$), 3.61 (3H, s, OCH$_3$) 3.62 (3H, s, OCH$_3$), 3.63 (3H, s, OCH$_3$), 3.78 (3H, s, OCH$_3$), 3.89 (3H, s, OCH$_3$), 4.50 (2H, s, —CH$_2$—), 6.28 (1H, d, J=12 Hz, —CH═CH—), 6.32 (2H, s, H-2, H-6), 6.42 (1H, d, J=9.0 Hz, H-5'), 6.52 (1H, d, J=12 Hz, —CH═CH—), 6.61 (1H, d, J=8.7 Hz, H-6'), 6.65 (1H, d, J=9.3 Hz), 6.74 (1H, d, J=8.1 Hz), 6.85 (1H, s), 7.81 (1H, d, J=6.6 Hz) 8.09 (1H, s).

Dosages

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/k of host body weight.

Expressed in terms of concentration, an active ingredient can be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filing operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration.

The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either phenstatin 3b and/or phenstatin prodrug 3d, and/or benzophenones 4a–f or any other compound described herein.

Composition "A"

Hard-Gelatin Capsules

One thousand two-piece hard gelatin capsules for oral use, each capsule containing 200 mg of an active ingredient are prepared from the following types and amounts of ingredients:

| Active ingredient, micronized | 200 g |
|---|---|
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient, are prepared from the following types and amounts of ingredients:

| Active ingredient, micronized | 200 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients:

| Active ingredient, micronized | 10 g |
|---|---|
| Citric acid | 2 g |
| Benzoic acid | 1 g |
| Sucrose | 790 g |
| Tragacanth | 5 g |
| Lemon Oil | 2 g |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

A sterile aqueous suspension for parenteral injection, containing 30 mg of an active ingredient in each milliliter for treating a neoplastic disease, is prepared from the following types and amounts of ingredients:

| Active ingredient, micronized | 30 g |
|---|---|
| POLYSORBATE 80 | 5 g |
| Methylparaben | 2.5 g |
| Propylparaben | 0.17 g |
| Water for injection, q.s. 1000 ml. | |

All the ingredients, except the active ingredient, are dissolved in the water and the solution sterilize by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| Active ingredient, micronized | 15 g |
|---|---|
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

One liter of a sterile aqueous suspension for intranasal instillation, containing 20 mg of an active ingredient in each milliliter, is prepared from the following types and amounts of ingredients:

| Active ingredient, micronized | 15 g |
|---|---|
| POLYSORBATE 80 | 5 g |
| Methylparaben | 2.5 g |
| Propylparaben | 0.17 g |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition "J"cl Insufflation

One hundred grams of an active ingredient in bulk form is finely divided by means of an air micronizer.

The foregoing composition is useful for treating a neoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a

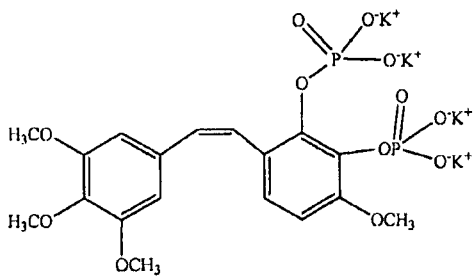

What is claimed is:

1. A compound of Formula I,

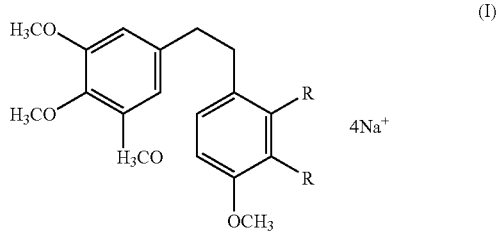

wherein:
X represents a cis-or trans-alkenyl or alkanyl group represented by $-(CH=CH)_1-$ or $-(CH_2-CH_2)_1-$;
at least one of $-OR_1$, $-OR_2$, $-OR_3$, or $-OR_4$ or $-O^+Q^-$, and the remainder are hydroxyl or $-O^+Q^-$; and
$Q^-$ is a metal or ammonium cation.

2. The compound of claim 1, wherein the metal cation is monovalent.

3. The compound of claim 2, wherein the monovalent metal cation is selected from the group consisting of lithium, sodium, potassium, and cesium.

4. The compound of claim 1, wherein the metal cation is divalent.

5. The compound of claim 4, wherein the divalent metal cation is selected from the group consisting of magnesium, calcium, manganese, and Zinc.

6. The compound of claim 1, wherein the ammonium cation is an alkaloid.

7. The compound of claim 6, wherein the alkaloid is selected from the group consisting of morpholine, piperazine, nicotinamide, quinine, quinidine, verapamil, and papaverine.

8. The compound of claim 1, wherein $-OR_1$, $-OR_2$, $-OR_3$, or $-OR_4$ are $-O^-Q^+$.

9. The compound of claim 1, wherein $-OR_1$ and $-OR_4$ are $-O^-Q^+$.

10. The compound of claim 1, wherein X is $-(CH=CH)_1-$.

11. The compound of claim 10, wherein X is in cis-conformation.

12. The compound of claim 11, wherein $O^-Q^+$ is $O^-Na^+$ or $O^-K^+$.

13. A pharmaceutical composition comprising a compound of claim 1 and a pharmaceutically acceptable carrier thereof.

14. A method for treating cells afflicted with a neoplastic disease, comprising administering to said cells an effective amount of the compound of claim 1.

15. The method of claim 14, wherein said cells are present in a mammal suffering said neoplastic disease.

16. The method of claim 15, wherein the neoplastic disease is selected from the group consisting of leukemia, lymphoma, ovarian cancer, central nervous system cancer, lung cancer, and colon cancer.

17. A compound having the following structure:

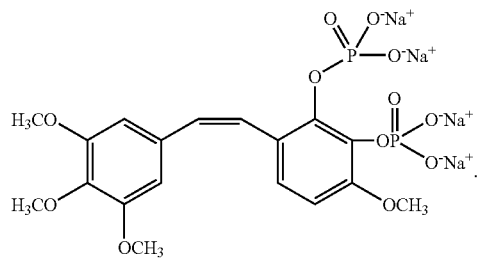

18. A compound having the following structure:

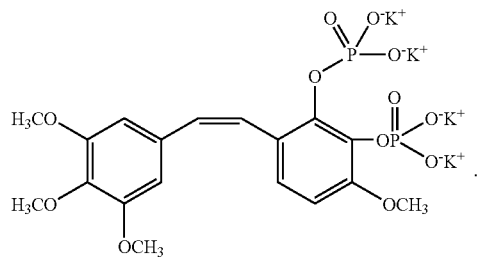

19. A compound having the following structure:

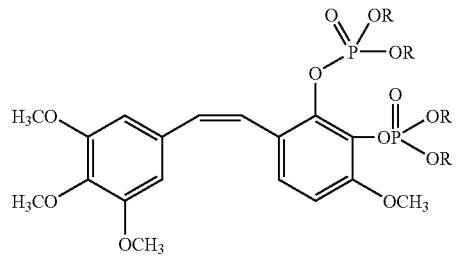

wherein R is selected from the group consisting of: lithium, potassium, calcium, magnesium, cesium, manganese, zinc, morpholine, piperazine, nicotinamide, quinine, quinidine, verapamil and papaverine.

20. A compound formed by the method comprising the steps of:
(a) providing Combretastatin A-1;
(b) reacting Combretastatin A-1 with a phosphorylation reagent; and
(c) reacting the compound of step (b) with a cleavage reagent.

21. The compound of claim 20, wherein the phosphorylation reagent is selected from the group consisting of dibenzyl phosphite, an alkylamidophosphine, or an alkylicyanophosphine.

22. The compound of claim 21, wherein the cleavage reagent is selected from the group consisting of trimethylislyl iodide, Raney nickel, ferric chloride, trimethylphenylthiosilane, chromium trioxide, a catalytic hydrogenation reagent, tripenylcarbenium, tin(IV) chloride, and lithium hydroxide.

23. A compound formed by reacting the composition of claim 20 with a salt comprising a metal or ammonium cation.

24. The compound of claim 23, wherein the metal cation is monovalent.

25. The compound of claim 24, wherein the monovalent metal cation is selected from the group consisting of lithium, sodium, potassium, and cesium.

26. The compound of claim 23, wherein the metal cation is divalent.

27. The compound of claim 26, wherein the divalent metal cation is selected from the group consisting of magnesium, calcium, manganese, and zinc.

28. The compound of claim 20, wherein the ammonium cation is an alkaloid.

29. The compound of claim 28, wherein the alkaloid is selected from the group consisting of morpholine, piperazine, nicotinamide, quinine, quinidine, verapamil, and papaverine.

30. A process for preparing a compound of claim 1 formed by the method comprising the steps of:
    (a) providing Combretastatin A-1;
    (b) reacting Combretastatin A-1 with a phosphorylation reagent;
    (c) reacting the compound formed in step (b) with a cleavage reagent; and
    (d) reacting the compound formed in step (c) with a salt comprising a metal or ammonium cation.

31. The process of claim 30, wherein the phosphorylation reagent is selected from the group consisting of dibenzyl phosphite, an alkylamidophosphine, or an alkylcyanophoshine.

32. The process of claim 31, wherein the cleavge reagent is selected from the group consisting of trimethylsilyl iodide, Raney nickel, ferric chloride, trimethylphenylthiosilane, chromium trioxide, a catalytic hydrogenation reagent, tripenylcarbenium, tin(IV) chloride, and lithium hydroxide.

33. The process of claim 30, wherein the metal cation is monovalent.

34. The process of claim 33, wherein the monovalent metal cation is selected from the group consisting of lithium, sodium, potassium, and cesium.

35. The process of claim 30, wherein the metal cation is divalent.

36. The process of claim 35, wherein the divalent metal cation is selected from the group consisting of magnesium, calcium, manganese, and zinc.

37. The process of claim 30, wherein the ammonium cation is an alkaloid.

38. The process of claim 37, wherein the alkaloid is selected from the group consisting of morpholine, piperazine, nicotinamide, quinine, quinidine, verapamil, and papaverine.

39. A compound having the following structure:

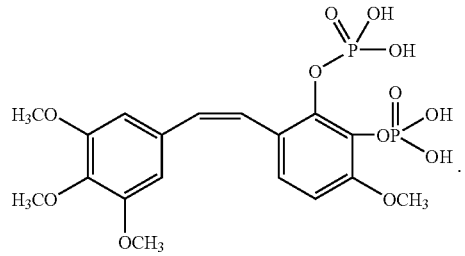

* * * * *

UNITED STATES PATENT AND TRADEMARK OFFICE
CERTIFICATE OF CORRECTION

PATENT NO.        : 7,078,552 B2                                    Page 1 of 1
APPLICATION NO.   : 10/258672
DATED             : July 18, 2006
INVENTOR(S)       : George R. Pettit et al.

It is certified that error appears in the above-identified patent and that said Letters Patent is hereby corrected as shown below:

Column 1, lines 17 and 18, "may have" should be changed to --has--.

Signed and Sealed this

Twenty-eighth Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,078,552 B2
APPLICATION NO. : 10/258672
DATED : July 18, 2006
INVENTOR(S) : Pettit et al.

It is certified that error appears in the above-identified patent and that said Letters Patent is hereby corrected as shown below:

- Column 23, line 6 claim 1, cancel the text beginning with "1. A compound of Formula I," and ending with "ammonium cation.", and insert the following claim:

-- 1. A compound of Formula I,

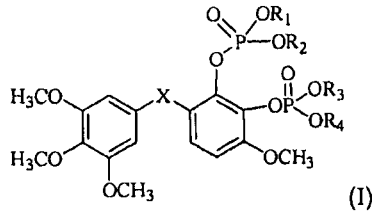

wherein:

X represents a *cis*- or *trans*- alkenyl or alkanyl group represented by $-(CH=CH)_1-$ or $-(CH_2-CH_2)_1-$;

at least one of $-OR_1$, $-OR_2$, $-OR_3$, or $-OR_4$ is $-O^-Q^+$, and the remainder are hydroxyl or $-O^-Q^+$;

and $Q^+$ is a metal or ammonium cation. --.

- Column 23, line 38, in claim 5, the text "Zinc" should be changed to -- zinc --.

- Column 23, line 51, in claim 11, the text "cis" should be -- *cis* --.

Signed and Sealed this

Thirty-first Day of August, 2010

David J. Kappos
*Director of the United States Patent and Trademark Office*

- Column 24, in claim 19, replace the chemical structure with the one shown below:

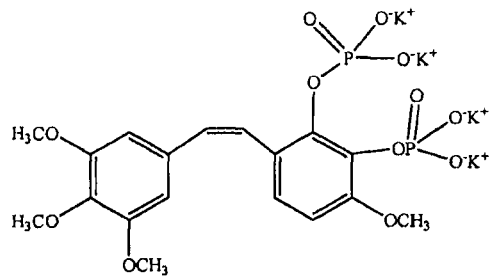

- Column 24, lines 53-54, in claim 21, the text "alkylicyanophosphine" should be changed to -- alkylcyanophosphine --.

- Column 24, lines 56-57, in claim 22, the text "trimethylislyl" should be changed to -- trimethylsilyl --.

- Column 25, line 26, claim 32, the text "cleavge" should be changed to -- cleavage --.

- Column 26, claim 39, replace the chemical structure with the one shown below: